(12) United States Patent
Olovson

(10) Patent No.: US 6,702,786 B2
(45) Date of Patent: Mar. 9, 2004

(54) NEEDLE PROTECTING ARRANGEMENT

(76) Inventor: Gudmar Olovson, 64 rue Saint-Charles, F-75015 Paris (FR)

( * ) Notice: Subject to any disclaimer, the term of this patent is extended or adjusted under 35 U.S.C. 154(b) by 0 days.

(21) Appl. No.: 10/182,207

(22) PCT Filed: Dec. 11, 2000

(86) PCT No.: PCT/SE00/02486
§ 371 (c)(1), (2), (4) Date: Jul. 23, 2002

(87) PCT Pub. No.: WO01/54759
PCT Pub. Date: Aug. 2, 2001

(65) Prior Publication Data
US 2002/0193749 A1 Dec. 19, 2002

(30) Foreign Application Priority Data
Jan. 25, 2000 (SE) ................................ 0000211

(51) Int. Cl.[7] .............................................. A61M 5/32
(52) U.S. Cl. ...................................... 604/198; 604/192
(58) Field of Search ............................... 604/192, 187, 604/198, 199, 263, 164.08

(56) References Cited

U.S. PATENT DOCUMENTS

| | | | | |
|---|---|---|---|---|
| 2,571,653 A | * | 10/1951 | Bastien | 604/192 |
| 4,425,120 A | * | 1/1984 | Sampson et al. | 604/198 |
| 4,631,057 A | * | 12/1986 | Mitchell | 604/198 |
| 4,725,267 A | * | 2/1988 | Vaillancourt | 604/195 |
| 4,801,295 A | * | 1/1989 | Spencer | 604/198 |
| 4,935,012 A | * | 6/1990 | Magre et al. | 604/192 |
| 5,024,616 A | * | 6/1991 | Ogle, II | 604/192 |
| 5,057,087 A | * | 10/1991 | Harmon | 604/198 |
| 5,647,849 A | * | 7/1997 | Kalin | 604/198 |
| 5,674,203 A | * | 10/1997 | Lewandowski | 604/197 |
| 5,735,823 A | * | 4/1998 | Berger | 604/192 |
| 5,843,047 A | * | 12/1998 | Pyrozyk et al. | 604/263 |
| 6,149,630 A | * | 11/2000 | Robinson | 604/198 |
| 6,537,257 B1 | * | 3/2003 | Wien | 604/198 |

FOREIGN PATENT DOCUMENTS

WO    WO 99/17822    * 4/1999

* cited by examiner

Primary Examiner—Sharon Kennedy
(74) Attorney, Agent, or Firm—Rolf Fasth; Fasth Law Offices

(57) ABSTRACT

The invention relates to a needle protection arrangement (2) for a hypodermic syringe (1), with a needle protector (2'). The hypodermic syringe (1) includes a container (10) and plunger (12), inside the container, to which a rod (11) imparts reciprocal motion and a needle (14) affixed to, or fastenable to, one end-part of the container. The needle protector (2) has a sealing membrane (2b) across its tubular cross-section at the opposite end from the container. The needle protector (2') has a first distinct position (100) prior to use and a second distinct and locked position (200) after use.

19 Claims, 1 Drawing Sheet

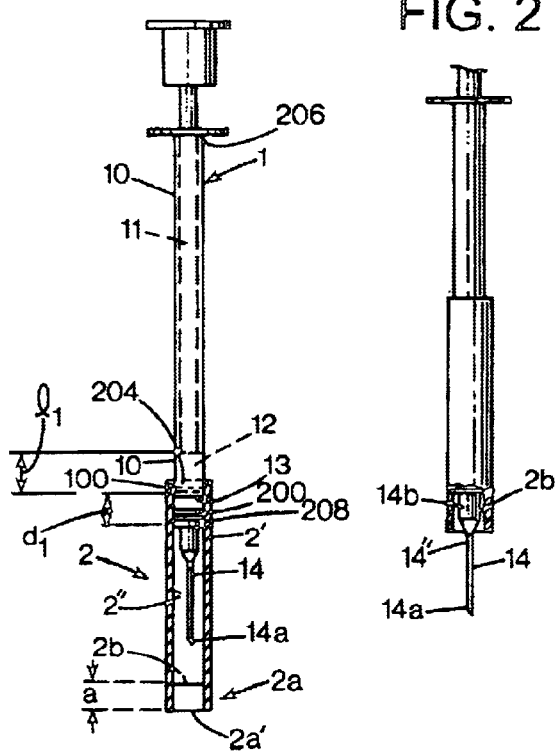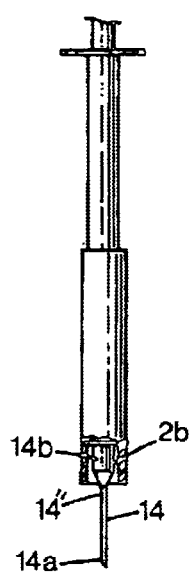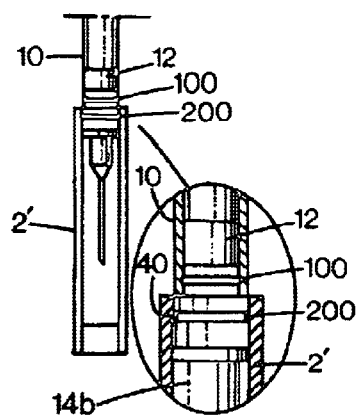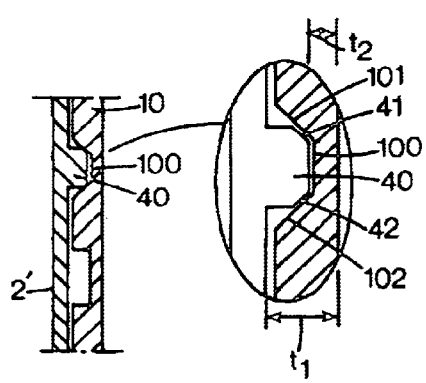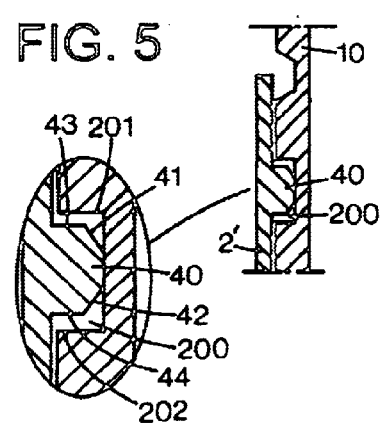

NEEDLE PROTECTING ARRANGEMENT

PRIOR APPLICATIONS

This application is a US national phase of International Application No. PCT/SE00/02486, filed Dec. 11, 2000, which claims priority from Swedish Application No. 0000211-3, filed Jan. 25, 2000.

TECHNICAL FIELD

The present invention relates to a needle protection arrangement for a hypodermic syringe.

BACKGROUND AND SUMMARY OF THE INVENTION

The needle protection arrangement of the present invention is being adaptable for co-action with a hypodermic syringe that includes a container, a plunger which can be moved reciprocatingly in said container by means of a rod and a needle which is affixed to or fastenable to one end-part of the container.

The invention is further based on said needle protection arrangement having a needle protector, basically in the shape of a tube, usually a circular, cylindrical tube whose axial length is slightly greater than the length of the needle.

More particularly, the present invention is devised for use with a needle protector in which the tube has an inner, radial-related cross-section corresponding to, or at least essentially corresponding to, an outer, radial-related cross-section for the container.

This cross-section dimensioning of the needle protector enables the device to be arranged for axial movement in relation to the container from a position in which the needle is covered by the device to a position in which the needle is exposed or vice-versa.

The invention relates more especially to such a needle protection arrangement in which the tubular needle protector's axial movement relative to the container can offer two distinctly separate setting positions, a first position in which the needle protector is devised to protect the needle and its point, the free end of the needle protector or tube end located next to the needle point, and a second position in which the needle protector is devised to protect the needle and with the free end of the needle protector or tube end located at a greater distance from the needle point while the needle protector covers the needle and its point, the first setting position being devised to initially pose stiff resistance to movement of the needle protector in relation to the container.

There has long been a wish to protect people who handle hypodermic syringes, used for injection and/or aspiration, against accidental injuries (prick injuries), and several different designs of needle protectors have been proposed to this end.

These needle protectors are usually movably or removably mounted to the container of the syringe and have an elongated shape enabling them in one position to cover the needle and the needle point.

The needle protector is removed prior to injection and/or aspiration so as to expose the needle and its point.

For the sake of simplicity, the following description is solely concerned with the injection of liquids, although it will be understood by anyone well-versed in the art that the concept 'injection' is equally applicable to aspiration.

A needle and needle point which remain exposed after an injection could become contaminated and thereby transmit serious illness to a person who is accidentally injured by the exposed needle and its needle point.

Various types of needle protectors which protect people against accidental injury are known to the art. Such protectors are basically in the form of a tube with a protective seal on the tube's free end.

A needle protector of this kind will have the form of a sleeve which can readily be removed from the syringe immediately prior to an injection. This sleeve must be kept separate during the injection process. After the injection the needle protector must be replaced by hand over the needle so as to shield the needle against unintentional contact therewith.

A needle protector sleeve of this kind is dimensioned at its open part for a secure but easily released co-action with the part of the needle attached to the container.

Other known needle protector constructions are movable over the container and co-act therewith during the injection, the injection syringe and the needle protector then forming a unit.

The present invention relates to the latter category of needle protection means.

Earlier known hypodermic syringe constructions with associated needle protection have been described and illustrated in the following patent publications:

U.S. Pat. No. 4,425,120 illustrates and describes a needle protector (19) which, in a first position, covers the needle (15) and the needle point (25) and, in a second, upwardly moved position, exposes the needle and the needle point.

The needle protector (19) is tubular which, at its free end, has a hole (41) large enough to allow a needle-holding means (24) or a needle protector (29) to pass through the hole.

The hole (41) may be covered with a material that is punctured by the needle (15) and/or the needle protector (29). The covering material is devised as a sealing end-region of the tubular needle protector and serves to seal the end-related edge or end surface of the tube.

U.S. Pat. No. 2,571,653 illustrates and describes a needle protector (1) which can be moved reciprocatingly between fixed positions, i.e., between a needle covering position and a needle exposing position. The free end of the needle protector (1) is conical and has a central opening which is devised to enclose the needle attachment (4).

The needle protector shown in U.S. Pat. No. 4,725,267 has an opening, i.e., a hole (58), and the free end (56) of the needle protector (60) is devised to correspond to the needle (14) cross-section.

A needle protector of the initially cited kind, described and disclosed in the international patent application no. PCT/SE98/01673 (WO99/17822), is also known.

More specifically, the invention relates to a construction in which the axial movement of the needle protector or tube in relation to the container has two distinct, separate setting positions, i.e., a first position in which the needle protector is devised to protect the needle and the needle point and with the free end of the needle protector located next to the needle point, and a second position in which the needle protector is devised to protect the needle and the needle point and with the free end of the needle protector located at a greater distance from the needle point while the needle protector covers the needle and its point, the first setting position being devised to initially pose stiff resistance to movement of the needle protector in relation to the container.

The contents of patent publication U.S. Pat. No. 4,801,295 are especially part of the prior art.

This publication illustrates and describes a needle protection arrangement for a hypodermic syringe.

It describes a hypodermic syringe with a needle protector which can be moved along the syringe container in order to assume a normal, first position in which the needle protector surrounds and protects the needle.

The needle is at least partially exposed in a second position on the container.

In a third position, the needle protector is moved to a needle-covering position and is locked and so firmly attached that it effectively prevents re-use.

FIG. 1 shows a position in which the needle protector is in its first position, FIG. 2 shows a position in which the needle protector exposes the needle for use, and FIG. 3 shows the needle protector in a third fixed position.

FIG. 4 further shows locking for the first position according to FIG. 1, FIG. 5 shows locking for the second position according to FIG. 2 and FIG. 6 shows locking for the third position according to FIG. 3.

It can then be seen that the position according to FIG. 4 has a recess 54 with a sloping surface 56 to facilitate needle protector 42 movement in relation to the container 32 in exposing the needle 38.

In the corresponding fashion, the position according to FIG. 5 shows a cavity 60 with a sloping surface for providing relative movement, whereas FIG. 6 depicts co-action with straight wall sections 64 in order to enclose the part 52 in blocking and locking the needle protector in the lower position.

Utilization of two parallel guide grooves 48 and 50 are shown here. They require the needle protector to be rotated in relation to the container in order to move the needle protector from the second position in the upper part of guide groove 48 to the third position in the lower part of the guide groove 50.

When taking into consideration the technical deliberations that a person skilled in this particular art must make in order to provide a solution to one or more of the technical problems that she/he encounters, it will be seen that, on the one hand, it is necessary initially to realize the measures, and/or sequence of measures that must be undertaken to this end, and, on the other hand, to realize which means is/are required to solve one or more of the said problems. On this basis, it will be evident that the technical problems listed below are relevant to the development of the present invention.

When the prior art, as described above and particularly illustrated and described in the initially cited international patent applications, is considered, it will be seen that a technical problem resides in devising a needle protector arrangement posing initially stiff resistance to movement of the needle protector from a distinct first position to a needle-exposing position, and after completed injection being able to bring the needle protector to a distinct second position after an injection position, thereby locking the needle protector in this position to the syringe container.

It will also be seen with a needle protection arrangement in which a utilized needle protector can assume one of two or three setting positions in relation to a container, that a technical problem resides in producing with simple means conditions in which the needle point can be readily released and exposed and then, after an injection, being able to re-cover the needle point by locking the needle protector or tube to the container.

It will also be seen that a technical problem resides in being able to realize the importance of and advantages associated with only letting the said second position be devised to offer the said locking of the needle protector in relation to the container.

It will also be seen that a technical problem resides in being able to realize the importance of and advantages associated with equipping the needle protector with a specially shaped locking boss designed to co-act with a container groove/grooves or vice-versa in order, in a first position, to pose stiff resistance to movement of the needle protector to a needle-exposing position, and in movement to a needle-covering position to be able to pass the said first position in moving the needle protector to a second needle-protection position and at which the needle protector is locked to the container.

It will also be seen that a technical problem resides in being able to realize the importance of and advantages associated with having slightly bevelled edges, or at least bevels facing a defined direction relative to the movement, on a locking boss in the needle protector arrangement.

It will also be seen that a technical problem resides in being able to realize the importance of and advantages associated with having a container groove with bevelled edges, or at least bevels facing one direction relative to the movement, in the said first position.

It will also be seen that a technical problem resides in being able to realize the importance of and advantages associated with having a container groove with squared-off edges, or at least edges facing one direction relative to the movement, in the said second position.

It will also be seen that a technical problem resides in being able to realize the importance of and advantages associated with creating conditions in which the needle protector or tube and container become inseparably conjoined in the said second position.

It will also be seen that a technical problem resides in creating, with simple means, conditions in which attempts to defeat locking, when the needle protector arrangement is in its second, locked position, primarily causes the container to break at the first position.

It will also be seen that a technical problem resides in creating conditions in which the fracture line is located next to and preferably immediately under the plunger when the plunger is in its lowest position.

It will additionally be seen that a technical problem resides in creating conditions in which, after the container has fractured following an attempt to defeat the locking arrangement, one part contains the needle, covered by the needle protector and with the needle protector locked in its second position, whereas the second part constitutes the larger part of the container with the fracture surface covered in whole or part by the plunger.

The present invention takes as its starting point a needle protection arrangement for a hypodermic syringe, comprising a needle protector in which the needle protector is devised to co-act with a syringe with a container, a plunger capable of reciprocal movement inside the container and a needle affixed to or fastenable to one end-part of the container, the said needle protector basically having the shape of a tube whose axial length is slightly greater than the length of the needle and which includes the features cited in the introduction in other respects.

The invention is also based on the circumstance that axial movement of the needle protector or tube in relation to the container shall have at least two, separate, distinct positions, i.e., a first position in which the needle protector or tube protects the needle and its needle point, the free end of the needle protector or tube located next to the needle point, and a second position in which the needle protector or tube protects the needle, the free end-part of the needle protector or tube being located at a greater distance from the needle point, while the needle protector covers the needle and its needle point, the said first needle position being devised to pose stiff resistance to movement of the needle protector or tube in relation to the container.

With the intention of solving one or more of the aforesaid technical problems, it is proposed in accordance with the present invention that the tube devised as a needle protector be arranged so the said second position provides locking and inseparable conjoining of the needle protector or tube in relation to the container, and the needle protector or tube is provided with a locking boss.

According to proposed embodiments that lie within the scope of the invention concept, it is proposed that the locking boss have somewhat bevelled edges.

In said first position, the container shall be provided with a groove having bevelled edges.

The container shall have a groove with transverse edges in the said second position.

The needle protector or tube and container are inseparably conjoined in the said second position.

The invention also proposes that any attempt to forcibly remove the needle protector from the container, when they co-act in the second position, will cause the container to fracture and destroy its injection capability.

The invention also proposes that this fracture produces one part in which the needle point and needle are covered by the needle protector and accordingly encapsulated, whereas the other part comprises the container, the open end-part of which is sealed by the plunger.

The main advantage regarded as characteristic of an arrangement for a syringe according to the present invention is that it thereby creates conditions for making a needle protector, using simple means, readily movable along the container of a hypodermic syringe.

Sliding the needle protector from a first position along the container to expose the needle and needle point for injection shall be easy.

After the syringe has been used, sliding the needle protector over the needle point, past the said first position to a second position in which the needle protector serves as permanent protection, the needle protector and the container being locked and inseparably conjoined in that second position, shall be possible.

Fracture scoring creates prerequisites.

The primary characteristic features of a needle protection arrangement for a hypodermic syringe according to the present invention are set forth in the characterizing clause of the following claim 1.

BRIEF DESCRIPTION OF THE DRAWINGS

One proposed embodiment, displaying the significant features of the present invention, will now be described in greater detail, referring to the enclosed drawings in which FIG. 1 shows a side view of a hypodermic syringe with a needle protector according to the invention in a first needle-protection position, FIG. 2 illustrates the syringe and needle protector, according to FIG. 1, in a position in which the needle protector has been slid back along the syringe container to expose the needle, FIG. 3 shows a side view of the hypodermic syringe with a needle protector according to the invention in a second needle-protection position after needle use, FIG. 4 is an enlarged view of the needle protector's co-action with the syringe container in a first position according to FIG. 1, and FIG. 5 shows an enlarged view of the needle protector's co-action with the'syringe container in a second, locked position according to FIG. 3.

DETAILED DESCRIPTION

FIG. 1 shows a side view of a hypodermic syringe 1 to which a needle protection arrangement 2 is attached according to the invention.

The hypodermic syringe 1 illustrated here has a container 10 with a rod 11 imparting reciprocating movement to a plunger 12 inside the container 10.

A needle 14 attached (or attachable for certain applications) to one end-part 13 of the container is also illustrated.

FIG. 1 shows that a needle protector 2 in the needle arrangement 2' has the basic shape of tube, with a circular cross-section, whose axial length is somewhat greater than the length of the needle 14.

The length shall be devised so the needle protector 2' covers both the needle 14 and one of the container's end-parts 13 and provides free access to the needle point 14a.

The needle protector 2' mainly consists of a tubular member 2' with an inner radial-related cross-section whose shape corresponds to, or at least essentially corresponds to, the shape of the container's 10 external radial-related cross-section.

The needle protector 2', in the form of e.g., the said tube 2', is axially movable in relation to the container 10 from a position covering the needle 14, according to FIG. 1, to a needle-exposing position, according to FIG. 2, or vice-versa.

At the end-part 2a facing away from the container 10, the needle protector 2' is provided with a thin membrane 2b sealing off the tube's inner cross-section.

'Thin membrane' 2b refers to a membrane thickness much less than the thickness of the tube 2' material.

The needle protector 2' consists essentially of a section of tubing with a circular cross-section and constant radius and a membrane 2b sealing/closing off the inner cross-section of the section of tubing.

The inner, circular surface 2" of the tube 2' is devised for light frictional co-action with the outer circular surface 10" of the container 10.

The said membrane 2b shall be made from a plastic material and of such a thickness that moving the tube 2' along the container 10 to expose the needle 14, according to FIG. 2, causes the needle point 14a to penetrate the said membrane 2b, thereby rendering the syringe 1 ready for use (according to FIG. 2), either for injection of a liquid in the container 10 or for aspiration of a liquid for analysis.

The properties of the membrane material should advantageously coincide with the properties of the material from which the tube is made, and it would be advantageous if the needle protector could be manufactured in a single operation.

The membrane 2b should advantageously have a thickness less than 0.5 mm, preferably between 0.1 and 0.3 mm, and the material should allow the needle point 14a to form an opening, whose peripheral edge region presses sealingly against the outer surface 14" of the needle 14.

The elasticity of the membrane material shall also enable the membrane 2b to stretch around the fastening part 14b of the needle 14, as shown in FIG. 2, without rupturing.

Referring to FIGS. 2 and 3, various alternative setting positions for the needle protector and the container will be described hereinafter in greater detail. However, please refer to the initially cited international patent applications, which can be regarded as part of the present invention, for a detailed account of the basic prerequisites for the present invention.

FIGS. 1 and 4 and 3 and 5 show that axial movement of the needle protector 2' or tube in relation to the container can assume two separate, distinct positions, a first position according to FIGS. 1 and 4 in which the needle protector or tube is devised to protect the needle and its needle point, the free end of the needle protector located next to the needle point, and a second position, according to FIGS. 3 and 5 in which the needle protector or tube protects the needle, the free end of the tube located at a greater distance from the needle point 14a while covering the needle 14 and its needle point 14a.

The said first position (FIG. 1) is devised to pose stiff initial resistance to movement of the needle protector 2' in relation to the container 10, small force then being required to move the needle protector 2' towards the position shown in FIG. 2. The first position is the position for an unused hypodermic syringe on delivery, and co-action between the needle protector and container is in the form of a snap fastening.

Even if the position according to FIG. 2 can be assumed to be a position for the needle protector in relation to the container, that position will not be the subject of further comment, as the needle protection arrangement assumes a position to expose the needle and its point and is, accordingly, not a protector in the sense the invention proposes.

More especially, it is proposed that the said second position (FIG. 3) be devised to provide locking of the needle protector 2' in relation to the container 10.

This locking means that even if considerable force is employed to move the needle protector on the container in the displacement direction, this force will be incapable of moving the needle protector 2' in relation to the container 10 without causing major material changes, changes so extensive that the syringe is rendered unusable.

More especially, the needle protector 2' and the container 10 are dimensioned so the unit is destroyed by the said force.

Efforts to force the hypodermic syringe by applying flexural force between the container and the needle protection arrangement will also lead to destruction of the entire syringe.

It may be appropriate to dimension the container 10 so it is bent by the breaking force at a recess devised for the first position.

The illustrated embodiment therefore proposes for this purpose that the needle protector 2' be provided with a locking boss 40.

The locking boss 40 shall have somewhat bevelled edges 41, 42.

In the said first position according to FIG. 4, the container 10 has a groove 100 with bevelled or rounded edges 101, 102 enabling the locking boss 40 to slide along and over the edges 101, 102 with some resistance.

In the said second position according to FIG. 5, the container 10 has a groove 200 with squared-off edges 201, 202, shown here as rectangular edges.

In the said second position, the needle protector 2' and the container 10 shall be inseparably conjoined. This is illustrated with bevels 41, 41 so narrow that the rectangular sections 43, 44 will abut the edges 201 and 202 respectively.

Devising the boss 40 with longitudinal length somewhat less than the distance between the surfaces 201, 202 may be appropriate.

In the position shown in FIG. 3, the groove can be positioned next to the upper part of the needle protector 2' and be covered somewhat by the said part.

Even if the embodiment shows that the needle protector 2' is provided with a boss 40 or an edge and the container 10 has a corresponding recess or groove, the container can be provided with the boss or edge and vice-versa It should be especially noted that if the syringe is subjected to a flexural force, the needle protector and lower part of the container should be devised and attached, as shown in FIG. 3, that fracture scoring appears at the groove 100 for the first position. This groove should be positioned a little below the plunger 12 and somewhat above the needle protector.

Breaking of the container at the recess 100 can form two parts, one enclosing the needle, its fastening and the lower part of the container. This part will be a closed unit with locking 200 between the needle protector and the container.

A second part will contain the upper part of the container, rod and descended plunger which serves as an end seal.

The invention is obviously not restricted to the exemplifying embodiment described above but can be modified within the scope of the invention concept as defined in the following claims.

What is claimed is:

1. A needle protection arrangement (2), including a needle protector (2°) and suitable for a hypodermic syringe, the syringe having a container (10) holding a rod (11) which imparts reciprocal motion to a plunger (12) in the container and a needle (14) affixed to or fastenable to one of the container's end-parts (13), the said needle protector (2') having the basic shape of a tube whose axial length is somewhat greater than the length of the needle, the tube serving as a needle protector with an inner radial-related cross-section shaped to correspond to or at least essentially correspond to the shape of the outer radial-related cross-section of the container (10), the said needle protector (2') being axially movable along the container from a needle-covering position to a needle-exposing position or vice-versa, the needle protector's axial movement in relation to the container offering at least two separate, distinct positions, a first distinct position in which the needle protector protects the needle (14) and its needle point, the free end of the needle protector being located adjacent to the needle point, and a second distinct position in which the needle protector protects the needle and its needle point, the free end of the needle protector being located at a greater distance from the needle point while the needle protector still covers the needle and its point, the first distinct position being devised to pose stiff resistance to movement of the needle protector in relation to the container in order to expose the needle point, wherein the first position is defined by a loose co-action of a locking boss (40) with a first recess or groove (100) in which the groove's (100) locking boss enclosing locking surfaces have opposing beveled or rounded edges (101, 102) so the locking boss (40) is able to slide, when there is movement in both directions, along and over the said rounded edges with some intentional resistance, that the said second position is defined by the co-action of the said locking boss (40) with an adjacent second recess or a groove (200) with transverse edges (201, 202) and that the second recess or groove pertaining to said second position being located closer to the needle (14) than the first recess or groove (100) for the first position, the container (10) having a constant first wall thickness (t1), except for the first and second grooves (100, 200), extending from a bottom end-part (204) to an under end-part (206), the container (10) having constant second wall thickness (t2) at the groove (100), the constant first wall thickness being greater than the constant second wall thickness.

2. A needle protection arrangement according to claim 1 wherein the needle protector is provided with a single locking boss facing the container.

3. A needle protection arrangement according to claim 1 wherein the locking boss is devised with somewhat beveled edges.

4. A needle protection arrangement according to claim 1 wherein the container has a transverse groove with beveled edges for the said first position.

5. A needle protection arrangement according to claim 1 wherein the container has a transverse groove with rectangular transverse edges for the said second position.

6. A needle protection arrangement according to claim 1 wherein the needle protector and container are inseparably conjoined in the said second position.

7. A needle protection arrangement according to claim 1 wherein a first end-part of the needle protector, facing away from a membrane disposed in the needle protector, is provided with a first part of a two-part coupling element between the needle protector and the container.

8. A needle protection arrangement according to claim 7, wherein the said first part is comprised of an inner radially and/or axially related groove or edge.

9. A needle protection arrangement according to claim 6, wherein a second part of a coupling element on the container consists of a radially and/or axially related edge or grove.

10. A needle protection arrangement according to claim 8 wherein the said edge is located next to the said end-part.

11. A needle protection arrangement according to claim 1 wherein the material in and the dimensioning of the needle protector, at least at the first end-part, has properties enabling the needle protector to expand over the said edge.

12. A needle protection arrangement according to claim 1 wherein a first needle protector end-part, facing away from the a membrane disposed in the needle protector, is provided with a first part of a two-part coupling arrangement, the container having two other coupling arrangement parts axially displaced from one other.

13. A needle protection arrangement according to claim 1 wherein a needle protector membrane (2b) is inside the needle protector 2' at a distance of 2 to 10 mm, preferably 3 to 5 mm, from the end of the tube.

14. A needle protection arrangement according to claim 1 wherein a membrane disposed in the needle protector is fastened to the needle protector by a ring-shaped reinforcement.

15. A needle protection arrangement according to claim 1 wherein the said needle protector is made from a transparent plastic material.

16. A needle protection arrangement according to claim 1 wherein the said first position groove serves as fracture scoring when a flexural force is imposed.

17. A needle protection arrangement according to claim 16 wherein the said fracture scoring groove is located, in the said second position, next to the fully inserted plunger inside the container.

18. A needle protection arrangement according to claim 1 wherein an end-part of the needle protector is located, in the said second position, next to the said grove.

19. A needle protection arrangement (2) comprising:

a needle protector (2');

a container (10) holding a rod which imparts reciprocal motion to a plunger (12) disposed in the container;

a needle (14) attachable to the container;

the needle protector (2') being tube shaped slidably mounted on the container from a needle-covering position to a needle-exposing position or vice-versa, the needle protector's axial movement in relation to the container providing at least two separate, distinct positions, a first distinct position in which the needle protector protects the needle (14), and a second position in which the needle protector is moved further away from the container, the first distinct position being devised to pose stiff resistance to movement of the needle protector in relation to the container in order to expose a needle point, wherein the first position is being defined by the loose co-action of a locking boss (40) with a first recess or groove (100) in which the groove's (100) locking boss enclosing locking surfaces have opposing beveled or rounded edges (101, 102) so the locking boss (40) is able to slide, when there is movement in both directions, along and over the rounded edges of the first groove (100) with some intentional resistance, that the second distinct position is being defined by a co-action of the locking boss (40) with a second groove (200) with transverse edges (201, 202) and that the second groove (200) is being located closer to the needle (14) than the first groove (100), the container (10) having a constant first wall thickness (t1), except for the first and second groove (100, 200), extending from a bottom end-part (204) to an upper end-part (206), the container (10) having a constant second wall thickness (t2) at the first and second grooves (100, 200), the constant first wall thickness being greater than the constant second wall thickness, the plunger (12) having a first sealing length (l1) that exceeds a distance (d1) extending from the first groove (100) to a container bottom (208).

* * * * *